US005726015A

United States Patent [19]
Matrisian

[11] Patent Number: 5,726,015
[45] Date of Patent: Mar. 10, 1998

[54] METHOD TO DETERMINE METASTATIC POTENTIAL OF TUMOR CELLS

[75] Inventor: Lynn M. Matrisian, Nashville, Tenn.

[73] Assignee: Vanderbilt University, Nashville, Tenn.

[21] Appl. No.: 371,082

[22] Filed: Jan. 10, 1995

Related U.S. Application Data

[63] Continuation of Ser. No. 61,827, May 17, 1993, abandoned, which is a continuation of Ser. No. 700,505, May 15, 1991, abandoned.

[51] Int. Cl.$^6$ ............................................. C12Q 1/68
[52] U.S. Cl. ................................................. 435/6; 536/23.5
[58] Field of Search ................................. 435/6, 7.1, 7.2; 536/23.5

[56] References Cited

U.S. PATENT DOCUMENTS

| | | | |
|---|---|---|---|
| 3,791,932 | 2/1974 | Schuurs et al. | 435/7.8 |
| 4,244,940 | 1/1981 | Jeong et al. | 436/500 |
| 4,376,110 | 3/1983 | David et al. | 435/5 |
| 4,677,058 | 6/1987 | Tryggvason et al. | 435/7.23 |
| 4,683,195 | 7/1987 | Mullis et al. | 435/6 |
| 4,808,528 | 2/1989 | Tryggvason et al. | 530/388.26 |
| 4,816,400 | 3/1989 | Tryggvason et al. | 435/219 |

FOREIGN PATENT DOCUMENTS

| | | | |
|---|---|---|---|
| 0237362 | 9/1987 | European Pat. Off. | C12Q 1/68 |
| 0297379 | 1/1989 | European Pat. Off. | C12Q 1/68 |
| 0300796 | 1/1989 | European Pat. Off. | C12Q 1/68 |
| 0310229 | 4/1989 | European Pat. Off. | C12Q 1/68 |
| 0328829 | 8/1989 | European Pat. Off. | C12Q 1/68 |
| 0329822 | 8/1989 | European Pat. Off. | C12Q 1/68 |
| 0369775 | 5/1990 | European Pat. Off. | C12Q 1/68 |
| 0371437 | 6/1990 | European Pat. Off. | C12Q 1/68 |
| 0373960 | 6/1990 | European Pat. Off. | C12Q 1/68 |
| 0379369 | 7/1990 | European Pat. Off. | C12Q 1/68 |
| WO88/10315 | 12/1988 | WIPO | C12Q 1/68 |
| WO89/06700 | 7/1989 | WIPO | C12Q 1/68 |
| WO89/07149 | 8/1989 | WIPO | C12P 19/34 |
| WO90/06376 | 6/1990 | WIPO | C12Q 1/68 |
| WO90/11358 | 10/1990 | WIPO | C12N 15/47 |

OTHER PUBLICATIONS

Collier et al., *J. Biol. Chem.*, vol. 263, 1988, pp. 6579–6587.
Garbisa et al., *Cancer Res.*, vol. 47, 1987, pp. 1523–1528.
Quantin et al., *Biochemistry*, vol. 28, 1989, pp. 5327–5334.
Muller et al., *Biochem. J.*, vol. 253, 1988, pp. 187–192.
Frohman et al., *PNAS*, vol. 85, 1988, pp. 8998–9002.
Document Number 07/194171 Inventor Stevenson et al.

Ausubel et al., In Current Protocols in Molecular Biology, John Wiley & Sons, pp. 16.8.1–16.11.7, supplement 10, 1990.
Basset et al., A Novel Metalloproteinase Gene Specifically Expressed in Stromal Cells of Breast Carcinomas, Nature 348:699–704 (Dec., 1990).
Harlow et al., Antibodies: A Laboratory Manual, Cold Spring Harbor Laboratory (pp. 53–138 for polyclonal antibodies, and 139–282 for monoclonal antibodies).
Harlow et al., Antibodies: A Laboratory Manual, Cold Spring Harbor Laboratory, pp. 555–612.
Kohler et al., Continuous Cultures of Fused Cells Secreting Antibody of Predefined Specificity, Nature 256:495–497 (1975).
Liotta et al., Metastatic Potential Correlates with Enzymatic Degradation of Basement Membrane Collagen, Nature 284:67–68 (1980).
Matrisian I, Metalloproteinases and Their Inhibitors in Matrix Remodeling, Trends in Genetics 6:121–125 (1990).
Matrisian et al. II, Stromelysin/Transin and Tumor Progression, Cancer Biol. 1:107–115 (1990).
Matrisian et al. III, The mRNA Coding for the Secreted Protease Transin is Expressed More Abundantly in Malignant than in Benign Tumors, Proc. Natl. Acad. Sci, USA 83:9413–9417 (1986).
McDonnell et al., Stromelysin in Tumor Progression and Metastasis, Cancer & Metastasis Reviews, 9:305–319 (1990).
Miyazaki et al., Purification and Characterization of Extracellular Matrix–Degrading Metalloproteinase, Matrin (Pump–1), Secreted from Human Rectal Carcinoma Cell Line, Cancer Res. 50:7758–7764 (1990).
Pajouh et al., Expression of Metalloproteinase Genes in Human Prostate Cancer, J. Cancer Res. Clin. Oncol., 117: (1991).
Woessner et al., Purification and Properties of a Small Latent Matrix Metalloproteinase of the Rat Uterus, J. Biol. Chem., 263:16918–16925 (1988).

*Primary Examiner*—James Ketter
*Attorney, Agent, or Firm*—Martin L. McGregor

[57] ABSTRACT

This invention relates to a method to determine the metastatic potential of tumor cells. In particular, this invention relates to the detecting of the expression of metalloproteinase pump protein. The expression of this protein can be determined by molecular diagnostic means such as a Northern Blot analysis or polymerase chain reaction amplification. Additionally, immunological methods can be employed to detect metalloproteinase pump protein.

7 Claims, 2 Drawing Sheets

METHOD TO DETERMINE METASTATIC POTENTIAL OF TUMOR CELLS

RELATED APPLICATIONS

This application is a Continuation of application Ser. No. 08/061,827 filed May 17, 1993, now abandoned, which is a Continuation of application Ser. No. 07/700,505 filed May 15, 1991, now abandoned.

The subject matter disclosed in this invention is sponsored by the American Cancer Society JFRA-192 and by the National Institutes of Health Grant No. CA 46853. This invention was made with Government support under Grant Number: CA 46853 awarded by NIH. The Government has certain rights in the invention.

BACKGROUND OF THE INVENTION

This invention relates to a method for the determination of the metastatic potential of tumor cells. In particular, this invention relates to a method to determine metastatic potential of tumor cells as a function of the expression of metalloproteinase pump protein.

DESCRIPTION OF THE PRIOR ART

One of the major characteristics of malignant cells is their ability to invade surrounding normal tissues and metastasize to distant body sites. It is the metastatic nature of malignant tumors that presents the greatest challenge to clinicians in terms of treatment, since the tumor is no longer localized to one area. Various combinations of surgery, radiation therapy and chemotherapy are available to the clinician, and the aggressiveness of the therapy is dependent in general on whether the tumor has invaded and metastasized. The presence of micrometastases, however, may be difficult to detect. This invention provides a tool that will aid in determining if a primary tumor has acquired the potential to invade surrounding tissue, which is an early event that is required for the formation of tumor metastasis.

Tumor invasion is a complex series of events, in which the tumor cells detach from the primary tumor, break down the normal tissue surrounding it, and migrate into a blood or lymphatic vessel to be carried to a distant site. The breaking down of normal tissue barriers is accomplished by the elaboration of specific enzymes that degrade the proteins of the extracellular matrix that make up basement membranes and stromal components of tissues.

A class of extracellular matrix degrading enzymes has been identified, called the matrix metalloproteinases. Two of the matrix metalloproteinases have been previously implicated in tumor invasion. The type IV collagenase has been correlated with the metastatic potential of tumor cells. Liotta et al., Nature 284;67–68 (March, 1980). The use of the production of this enzyme by tumor cells as a diagnostic tool has been disclosed in U.S. Pat. Nos. 4,677,058; 4,808,528; 4,816,400. Additionally, it has been shown that the production of the matrix metalloproteinase stromelysin is associated with malignant tumors with metastatic potential. Matrisian and Bowden, Smnrs. in Cancer Biology, 1:107–115 (1990). McDonnell and Matrisian, Cancer and Metastasis Reviews 9:305–319 (1990).

The pump cDNA clone was originally isolated by Richard Breathnach and his colleagues from a cDNA library prepared from mRNA from a collection of human tumor cells. Muller et al., Biochem. J. 253:187–192 (1988). There is no indication in this publication as to the type of tumor that expresses pump enzyme, whether it is found in normal tissue, or if there is any relationship between tumor invasion and metastasis and pump expression. A subsequent publication by this group (Quantin et al., Biochemistry 28:5327–5334, (1989)) confirms that the pump protein is a metalloproteinase and can degrade extracellular matrix and basement membrane proteins.

The present invention relates to the determination that the pump enzyme is associated with tumor invasion and metastasis in human gastric and colon cancer. Since our initial observation that pump mRNA is expressed in human colon and gastric tumors, Miyazaki et al. (Cancer Research 50:7758–7764 (1990)) have reported the expression of pump protein, which is named matrin, in a human rectal carcinoma cell line. Additionally, Basset et al. (Nature 348:699–704 (1990)) have reported the expression of pump mRNA in seven out of ten primary human breast carcinomas. Neither of these investigators has examined a correlation between metastatic potential and pump mRNA or protein expression.

SUMMARY OF THE INVENTION

It is the object of the present invention to provide methods to determine the metastatic potential of tumor cells. In particular, this application deals specifically with using the production of pump mRNA by the tumor cells as a diagnostic tool to determine the probability that that tumor is invasive, and thus, aid in evaluating the aggressiveness of the therapy that is used to treat the patient. Additionally, it is an object of this invention to determine metastatic potential of tumor cells as a function of the expression of metalloproteinase pump proteins by said cells comprising:

a. obtaining a sample of tumor cells;
  b. detecting mRNA to the pump proteins in the sample;
  c. comparing the detected mRNA with mRNA in noncancerous tissue; and
  d. determining metastatic potential of the tumor cells based on the comparison.

Another objective of this invention is to provide a method to determine metastatic potential of tumor cells as a function of the presence of mRNA to metalloproteinase pump proteins in a biological sample comprising: obtaining a sample of tumor cells; extracting mRNA from the tumor cells; reverse transcribing to mRNA to obtain cDNA; amplifying cDNA; and quantitating the amplified product by radiometric, fluorometric, colorimetric, densitometric or photometric measurements.

Yet another object of this invention is a method to determine metastatic potential of tumor cells comprising: immunologically detecting metalloproteinase pump protein.

In particular, this invention is directed to the determination of the metastatic potential of gastric or colon cancer.

DETAILED DESCRIPTION OF THE INVENTION

Our observation that pump mRNA is produced by human gastric and colon tumors and the lack of expression in normal noncancerous tissues has lead to the identification of pump mRNA expression as a diagnostic tool for tumor invasion.

Figure 1:
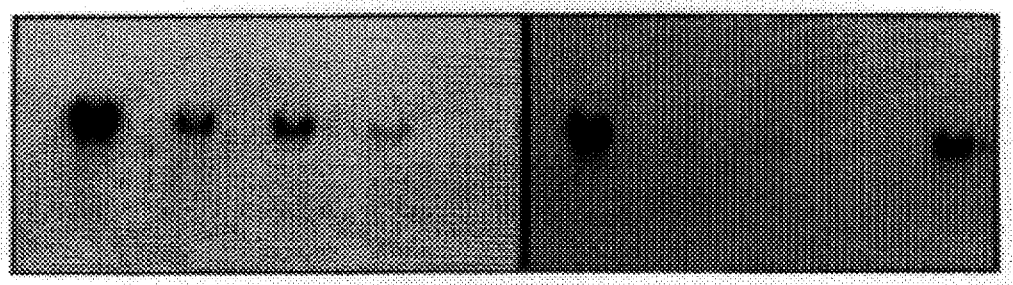
FIG. 1 shows the autoradiogram from a Northern Blot analysis of primary gastric tumor samples probed with pump.
Figure 2:
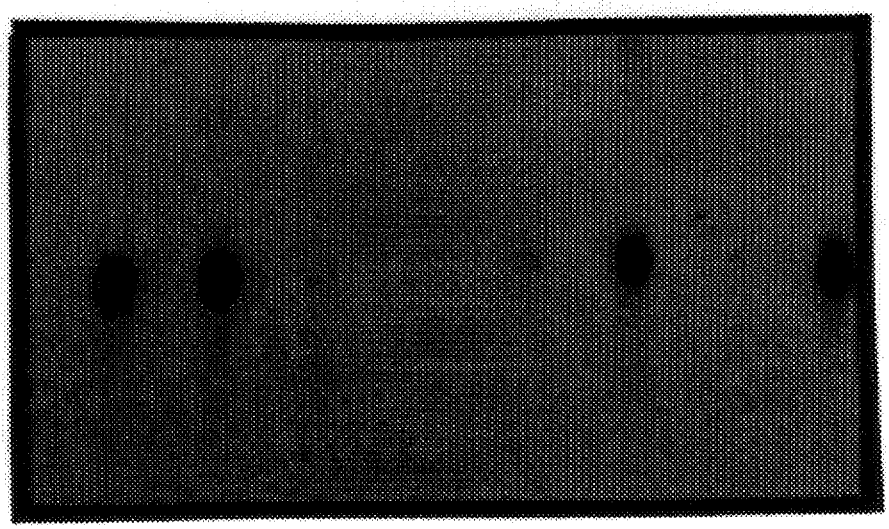
FIG. 2 shows the autoradiogram from a Northern Blot analysis of primary colon tumor samples probed with pump.

A series of human gastric and colon carcinomas and adjacent uninvolved tissue were obtained from the Department of Surgical Pathology, Vanderbilt University. Poly(A) +RNA was isolated from these samples and assayed by Northern Blot analysis for the expression of transcripts hybridizing to the human pump cDNA probe. In ten paired samples of primary gastric carcinomas and normal adjacent tissue, pump mRNA was detectable in eight out of ten carcinomas and was not detected in any of the normal tissue samples (FIG. 1). In FIG. 1, N indicates mRNA from normal tissue and C indicates mRNA from cancer tissue. In a similar study with normal and colon carcinoma samples, high levels of pump mRNA was detected in four out of eight carcinomas, and low levels in two additional carcinomas (FIG. 2). Pump mRNA was not detectable in any of the normal tissue samples.

Information regarding the size of the primary tumor and presence or absence of lymph node metastases was available for the ten gastric carcinomas examined. This data is compared with the relative levels of pump mRNA in Table I. There is no correlation between the size of the primary tumor and pump mRNA expression. Pump mRNA was present in six out of seven tumors for which lymph node metastases were detected. In one tumor with no evidence of lymph node metastases, pump mRNA was not detected. There is therefore a correlation between expression of pump mRNA and the ability of the primary tumors to metastasize. Based on these data and the proteolytic activity of pump protein for extracellular matrix components, the expression of pump mRNA or protein may be an indicator of the potential of a primary tumor to metastasize. This suggests that the two tumors that displayed low levels of pump mRNA, but for which lymph node metastases were not detected, had the potential to metastasize and should be treated as such. The absence of pump expression, however, does not rule out the possibility that the tumors can metastasize, since occasionally the elaboration of other, nonpump-related proteases may facilitate metastasis in these tumors.

TABLE I

| ID | AGE | SEX | PRIMARY TUMOR SIZE (mm) | METASTASES positive nodes/ # of nodes examined | PUMP LEVELS |
|---|---|---|---|---|---|
| 1 | 83 | M | 10 × 6 × 5 | 1/22 | +++ |
| 2 | 61 | M | 7 × 5 × 1.3 | 7/15 | ++ |
| 3 |  | M | 7.5 × 7 | 2/6 | ++ |
| 4 | 33 | M | 3.5 × 1.5 | 3/17 | + |
| 5 | 73 | M | 8.5 × 5.5 × 5 | neg | none |
| 6 |  | M | 12 × 8.5 × 6 | 1/64 | +++ |
| 7 | 58 | M | 8 × 7 × 2 | neg | + |
| 8 | 70 | M | 6.2 × 2.8 × 2.5 | neg | + |
| 9 | 73 | M | 10 × 4.5 | 1/6 | none |
| 10 | 77 | M | 3.5 × 3 × 1.5 | 1/5 | +++ |

Characteristics of human gastric tumors analyzed for pump mRNA levels. For each sample analyzed for pump mRNA, the age (in years) and sex (M=male) of the patient is indicated, the approximate size of the primary tumor in mm, the number of lymph nodes containing metastatic nodules, and the relative pump mRNA level (from data shown in FIG. 1).

The expression of pump mRNA in human tumors can be detected in a number of ways. A Northern Blot analysis can be conducted. Other mechanisms relating to amplification can be used to detect pump mRNA.

Several methods have been disclosed to amplify the desired nucleic acid sequence to a sufficient concentration for detection. In particular, Mullis et al., U.S. Pat. No. 4,685,195 (incorporated by reference) disclose a technique known as polymerase chain reaction (P.C.R.) for amplifying and detecting any target nucleic acid sequence. In PCR separate complementary strands of the nucleic acid are treated with an excess of two oligonucleotide primers. The primers are extended to form complementary primer extension products which act as templates for synthesizing the desired nucleic acid sequence and the amplified sequence is then detected.

This process has been applied to the detection of mRNA in a biological sample, by extracting mRNA, reverse transcribing the mRNA to DNA, and amplification of the DNA by polymerase chain reaction. Specifically, the technique can be used to measure the expression of oncogenes and enzyme markers involved in tumor invasion and metastasis. Stevenson, U.S. Pat. No. 7,194,171, (incorporated by reference).

Other nucleic acid amplification techniques are useful for detecting the presence of metalloproteinase pump mRNA. See, e.g. Adams, C. W. U.S. Pat. No. 4,888,058, Single-Stranded Self Hybridising Nucleic Acid Probe Capable of Repeatedly Hybridising to Itself or Other Nucleic Acids to Form an Amplified Entity; Erlich et al., EP 237,362, Detection of Specific Nucleotide Variations in Nucleic Acids-by Hybridising with Nucleotide Triphosphates, and polymerizations Agent, Separating into Single Strands and Amplifying; Gingeras T., WO8810315, Transcription-based Nucleic Acid Amplification-Using Nucleic Acid Primers Corresponding to a Segment of a Target Sequence and Polymerase Extension; DaHagupta, N., EP 297,379, Amplifying Specific Target Nucleic Acid Sequence-by Hybridization with two Immobilized or Immobilizable Primers and Extension Using an Enzyme; Becker, M., WP 300,796, Amplification in Polynucleotide Assays-by Extension Using Nucleotide Triphosphate(s) and Template-Dependent Polynucleotide Polymerase, Cleavage and Dissociation; Burg, L., WO 310,229, Amplification of Target Polynucleotide Sequences-by Hybridizing with Primer Containing Promoter, Producing DNA Intermediate and Growing Multiple RNA Copies; Davey C., EP 329,822 Amplification of Specific Nucleic Acid Sequence- Using RNA and DNA Polymerase(s) on Single Stranded RNA, Single Stranded and double Stranded Templates; Sommer, S., WO 8907149, Genomic Amplification with Direct Sequencing- With Hybridization of Oligo-Nucleotide Primers, at Least One Containing Promoter, to Each End of a DNA Sequence; Collins, M., EP 328,829 Assays for Target Polynucleotide(s) by Isolation From Extraneous Non-Target Polynucleotide(s) and Impurities and Amplification; Miller, H., WO 8906700, Detection of Specific Nucleic Acid Sequence in Sample-by Detecting RNA Transcripts Synthesized from Nucleic Acid which Includes the Sequence Ribonucleic; Chu et al., WO 9006376, Co-Functional Nucleotide Sequences used with RNA Dependent RNA Polymerase as Amplification System for Detecting Target RNA; Gingeras et al. EP 373,960 Amplification of RNA Sequences by using Primer Containing Polymerase Binding Site; Solderland et al., EP 371,437 Detection of Sequence of Target Nucleic Acid by Amplification and Immobilization Through Attachment Moiety to Attachment Sites on Support; Loewy et al., EP 369,775 Mobile Promoter Structure for Amplification of Target Sequence—Comprising Two Promoters Containing Polynucleotide Strands, One also Containing Probe Sequence to form Complex with Target; Rose et al., EP 379,369 Nucleic Acid Amplification using Single Primer—by Forming Along Poly-Nucleotide Extension of Single Poly-Nucleotide Primer, then Dissociating (all incorporated by reference).

Additionally, immunological tests for tumor invasion can be described. The isolation and purification of pump enzymes makes it possible to produce specific antibodies to this enzyme. The production of these antibodies facilitates the development of immunological tests for tumor invasion by the qualitative or quantitative determination of metalloproteinase pump antigens in a biological sample.

The techniques for the preparation of polyclonal or monoclonal antibodies are well known. Kohler and Milstein, Nature, Vol. 256, p. 496 (1975). Similarly, the use of antibodies in diagnostic tests is well known. Schuurs et al., U.S. Pat. Nos. 4,244,940, 3,791,932; and David et al., 4,376,110.

Pump protein can be expressed and purified by a number of standard procedures. Expression systems could utilize mammalian or insect tissue culture systems, or prokaryotic cells. For example, the full-length pump cDNA could be inserted into the expression vector pKCR6 and stably transfected into Chinese Hamster ovary cells with a mutant dihydrofolate reductase gene. Plasmid-containing cells can then be selected in selection medium and the integrated plasmid amplified with methotrexate as has been previously described for the production of the related protein stromelysin/transin. Matrisian et al., Proc. Natl. Acad. Sci. USA 83:9413–9417 (1986). The baculoviral expression system for production of large amounts of protein in cultured insect cells is well established and could be utilized for the purpose of producing pump protein. Ausubel, F. M., Brent, R., Kingston, R. E., Moore, D. D., Seidman, J. G., Smith, J. A., and Struhl, K., in Current Protocols in Molecular Biology, John Wiley & Sons, pgs. 16.8.1–16.11.7, supplement 10, 1990. Pump protein could also be expressed as lacZ, trpE, or glutathione-s-transferase fusion proteins in an E. coli host system according to established procedures. Ausubel, F. M., Brent, R., Kingston, R. E., Moore, D. D., Seidman, J. G., Smith, J. A., and Struhl, K., in Current Protocols in Molecular Biology, John Wiley & Sons, pgs. 16.0.3–16.7.8, supplement 10, 1990.

Pump protein can be purified from these sources by standard protein purification procedures. Examples of purification of pump or pump-like proteins from biological sources has been published. Woessner, J. F. Jr., and Taplin, C. J., J. Biol. Chem. 263:16918–16925 (1988). Miyazaki et al., Cancer Res. 50:7758–7764 (1990).

Either polyclonal or monoclonal antibodies can be generated to purified pump protein using standard procedures. Harlow, E., Lane, D., eds., Antibodies: A Laboratory Manual, Cold Spring Harbor Laboratory (pgs. 53–138 for polyclonal antibodies, and 139–282 for monoclonal antibodies).

Standard assays for detection of proteins with either polyclonal or monoclonal antibodies include antibody capture assays and two-antibody sandwich assays. Protocols for such assays have been described. Harlow, E., Lane, D., eds., Antibodies: A Laboratory Manual, Cold Spring Harbor Laboratory, pgs. 555–612.

EXAMPLE 1

A small sample of the primary tumor was acquired at the time of surgery. The tumor RNA was isolated as follows:

Samples of gastric carcinoma and adjacent normal tissue were obtained from the Department of Surgical Pathology, Vanderbilt University. Total cellular RNA was prepared by disrupting the tumor with a Tissumizer (Tekmar, Inc.) in 4M guanidinium isothiocyanate, 5 mM sodium citrate, 0.1M beta-mercaptoethanol, 0.5% sarkosyl and pelleting the RNA through a cushion of 5.7M CsCl/0.1M EDTA. Poly(A)+ RNA was selected using oligo d(T) cellulose and eluted in HI salt buffer (10 mM Tris-HCl, pH 7.4), 0.4M NaCl, 1 mM EDTA, 0.2% sodium dodecyl sulfate). Poly(A)+RNA (5 µg) was separated on a 1.2% agarose gel containing 2.05M formaldehyde in a buffer containing 20 mM MOPS, 3 mM sodium acetate, and 1 mM EDTA, pH 7.6. The RNA was transferred to nitrocellulose paper and hybridized to a random-primed cDNA probe (1.2 kB EcoRI fragment from pPUMP-1. The pump-1 cDNA has the following nucleotide sequence: AAGAACAATTGTCTCTGGACGGCAGC-TATGCGACTCACCGTGCTGTGTGCTGT-GTGCCTGCTGCC TGGCAGCCTGGCCCTGCCGCT-GCCTCAGGAGGCGGGAGGCATGAGTGAGCTACAG-TGGGAACAGG CTCAGGACTATCTCAAGAGATTT-TATCTCTATGACTCAGAAACAAAAAAT-GCCAACAGTTTAGAA GCCAAACTCAAGGAGATG-CAAAAATTCTTTGGCCTACCTATAACTGGAATGTTA-AACTCCCGCGT CATAGAAATAATGCAGAAGCCCA-GATGTGGAGTGCCAGATGTTGCA-GAATACTCACTATTTCCAA ATAGCCCAAAATG-GACTTCCAAAGTGGTCACCTACAGGATCGTATCAT-ATACTCGAGACTTACCG CATATTACAGTGGATC-GATTAGTGTCAAAGGCTTTAAACAT-GTGGGGCAAAGAGATCCCCCTGCA TTTCAG-GAAAGTTGTATGGGGAACTGCTGACATCATGATTG-GCTTTGCGCGAGGAGCTCATGGGG ACTCCTAC-CCATTTGATGGGCCAGGAAACACGCTG-GCTCATGCCTTTGCGCCTGGGACAGGTCTC GGAG-GAGATGCTCACTTCGATGAGGATGAACGCTGGACG-GATGGTAGCAGTCTAGGGATTAACTT CCTGTAT-GCTGCAACTCATGAACTTGGCCAT-TCTTTGGGTATGGGACATTCCTCTGATCCTAATG CAGTGATGTATCCAACCTATGGAAATG-GAGATCCCCAAAATTTTAAACTTTC-CCAGGATGATATT AAAGGCATTCAGAAACTATATG-GAAAGAGAAGTAATTCAAGAAAGAAATAGAAACTT. Muller et al., Biochem. J. 253:187–192 (1988), labeled with $^{32}$P-dCTP and the Random Primed DNA labeling kit, Boehringer Mannheim, Inc.) in the presence of 50% formamide, 5×SSC (1×SSC=0.015M sodium citrate/0.15M NaCl, pH 7.0), 1×Denhardts solution, 20 mM sodium phosphate, 0.1% sodium dodecyl sulfate, 50 µg/ml salmon sperm DNA and 4% dextran sulfate at 42° C. The filters were washed following a 10 hour hybridization in 0.1×SSC and 0.1% sodium dodecyl sulfate at 50° C. and exposed to X-ray film using an intensifying screen. Samples from individual patients are identified by a number as indicated in Table 1. N=normal adjacent tissue, C=carcinoma. Results of this study, shown in FIG. 1, reveal the presence of pump mRNA in 80% of gastric tumors examined.

Samples of colon carcinoma and adjacent normal tissue were obtained and analyzed for pump mRNA as described above. Samples from individual patients are identified by number, N=normal tissue, C=carcinoma. Results of this study, shown in FIG. 2, reveal pump mRNA in 75% of colon tumors examined.

EXAMPLE 2

Poly(A)+RNA (1 µg) isolated from normal (N) or carcinoma (C) tissue from patients #1 and 2 as indicated in FIG. 2 was incubated with 400 units of Moloney-murine leukemia virus (M-MLV) reverse transcriptase in the presence of 50 mM Tris-HCl, pH 8.3, 50 mM MgCl$_2$, 10 mM dithiolthreitol, 75 mM KCl, 0.5 lg oligo d(T), 0.5 mM each dNTP, 40 units RNasin™ (Promega, Inc.) at 37° C. for 1 hour. One sixth of this cDNA sample was mixed with 2.5 units of Taq polymerase (AmpliTaq™, Perkin Elmer Cetus)

in the presence of 10 mM Tris-HCl, pH 8.3, 1.5 mM $MgCl_2$, 50 mM KCl, 0.2 mM each dNTP and 0.001% (w/v) gelatin. Two oligonucleotides (1.2 μM final concentration) with the following sequence were added: 5'TGTATCCAACCTATG-GAAATG 3', 5' CATTTATTGACATCTACGCGC 3'. The reaction was denatured at 94° C. for 1.5 minutes, annealed at 54° C. for one minute, extended at 72° C. for three minutes. The cycle was repeated 30 times, followed by an extension at 72° C. for seven minutes. One half of the reaction was then restricted for one hour at 37° C. with XmnI (Promega, Inc.) in the buffer supplied with the enzyme. The undigested (U) and digested (D) reaction products were separated by electrophoresis on a 1.5% agarose gel in 50 mM Tris-borate, pH 8.3 and 1 mM EDTA. The DNA was stained with ethidium bromide and photographed under UV illumination.

Figure 3:
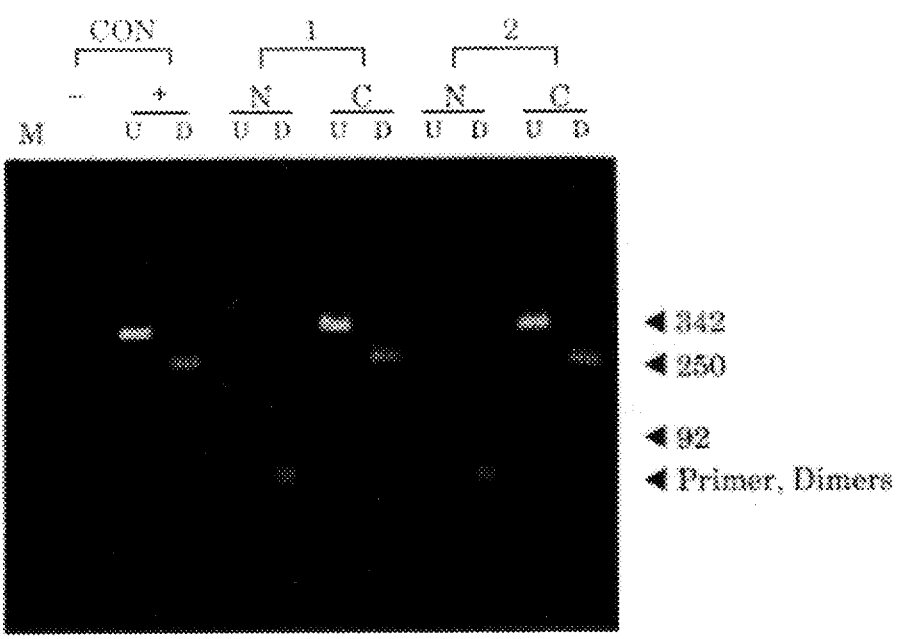
FIG. 3 shows electrophoretic patterns of a PCR amplified fragments from RNA isolated from gastric tumor samples.

The results are shown in FIG. 3 and are interpreted as follows:

a. The presence of a band at 342 base pairs indicates the presence of pump mRNA in the tumor sample.

b. The presence of two bands at 250 and 92 base pairs following XmnI digestion confirms the identity of the amplified fragment as originating from pump sequences. See FIG. 3, lanes D.

We have verified the results of this assay using mRNA isolated from human tumor samples that were determined to be positive for pump expression by Northern Blot analysis. Carcinoma samples from two patients that demonstrated pump RNA by Northern Blot analysis (FIG. 2, patient #1 and #2) also demonstrated the specific amplified fragment when subjected to RT-PCR (342 base pairs) (FIG. 3). XmnI digestion of this fragment into two fragments of 250 and 92 kilobases confirmed the identity of this fragment as originating from pump cDNA (FIG. 3). Appreciable amounts of amplified fragment was not detected by the PCR assay in normal samples for which pump mRNA was not detected by Northern Blot analysis (FIG. 2).

The PCR assay could be modified to be quantitative by the addition of plasmid DNA to the PCR reaction containing the pump cDNA with a mutation that creates a unique EcoRI site within the XmnI site in the region of the pump cDNA that is amplified by the primers. The presence of two bands at 254 and 88 base pairs following EcoRI digestion would serve as an internal control to compare the level of amplification of both plasmid and cDNA in each sample and would serve as an indicator that the PCR reaction was effective. This approach for quantitation of PCR reactions has been used successfully by Gilliland et al. Gilliland et al., in PCR Protocols: A Guide to Methods and Applications, M. A. Innis, G. H. Gelfand, J. J. Sninsky, T. J. White, eds., Academic Press, Inc., pp. 60–69, 1990.

While the present invention has been described by reference to certain illustrative examples, various modifications and variants within the spirit and scope of the invention will be apparent to those skilled in the art.

I claim:

1. A method to determine whether tumor cells will metastasize by detecting the expression of metalloproteinase pump-1 mRNA by said tumor cells, the method comprising the steps of:

a. obtaining a sample of tumor cells and a sample of non-cancerous cells adjacent to said tumor cells;

b. detecting mRNA to metalloproteinase pump-1 proteins in tumor cells and in non-cancerous cells;

c. comparing the detected pump-1 mRNA in the tumor cells with the pump-1 mRNA in the non-cancerous cells; and d. Determining whether the tumor cells will metastasize by detection of a higher level of pump-1 mRNA in the tumor cells than in the non-cancerous cells.

2. The method of claim 1 wherein said tumor cells are selected from the group consisting of gastric cancer and colon cancer.

3. A method to determine whether tumor cells will metastasize by detecting the expression of metalloproteinase pump-1 mRNA by said tumor cells, the method comprising the steps of:

a. obtaining a sample of tumor cells;

b. extracting mRNA from said tumor cells;

c. reverse transcribing said mRNA to obtain cDNA;

d. amplifying said cDNA corresponding to pump-1 RNA;

e. quantitating the amplified product; and f. Determining whether the tumor cells will metastasize by detection of a higher level of pump-1 mRNA in the tumor cells than in non-cancerous cells in surrounding tissue.

4. The method of claim 3 wherein said tumor cells are selected from the group consisting of colon cancer and gastric cancer.

5. A method according to claim 3 wherein the quanitation of the amplified product is carried out by radiometric, flurometric, calometric, densiometeric or photometeric measurements.

6. An early detection method for metastatic tumors which comprises determining the expression level of metalloproteinase pump-1 in a sample from a tumor and in a sample of normal tissue and comparing the determined levels of pump-1 expression wherein metastatic tumors express a higher level of metalloproteinase pump-1 than normal tissue.

7. The method of claim 6 which further comprises the steps of:

a. obtaining a sample of tumor cells and a sample of non-cancerous cells adjacent to said tumor cells;

b. detecting mRNA to metalloproteinase pump-1 or the metalloproteinase pump-1 protein in tumor cells and in non-cancerous cells;

c. comparing the detected pump-1 mRNA or pump-1 protein in the tumor cells with the pump-1 mRNA or pump-1 protein in the non-cancerous cells.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 837 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA- -
        ( ( iii) HYPOTHETICAL: NO ( i v ) ANTI-SENSE: NO ( x i ) SEQUENCE DESCRIPTION: SEQ ID NO: 1:

```
AAGAACAATT  GTCTCTGGAC  GGCAGCTATG  CGACTCACCG  TGCTGTGTGC   50

TGTGTGCCTG  CTGCCTGGCA  GCCTGGCCCT  GCCGCTGCCT  CAGGAGGCGG  100

GAGGCATGAG  TGAGCTACAG  TGGGAACAGG  CTCAGGACTA  TCTCAAGAGA  150

TTTTATCTCT  ATGACTCAGA  AACAAAAAAT  GCCAACAGTT  TAGAAGCCAA  200

ACTCAAGGAG  ATGCAAAAAT  TCTTTGGCCT  ACCTATAACT  GGAATGTTAA  250

ACTCCCGCGT  CATAGAAATA  ATGCAGAAGC  CCAGATGTGG  AGTGCCAGAT  300

GTTGCAGAAT  ACTCACTATT  TCCAAATAGC  CCAAAATGGA  CTTCCAAAGT  350

GGTCACCTAC  AGGATCGTAT  CATATACTCG  AGACTTACCG  CATATTACAG  400

TGGATCGATT  AGTGTCAAAG  GCTTTAAACA  TGTGGGGCAA  AGAGATCCCC  450

CTGCATTTCA  GGAAAGTTGT  ATGGGGAACT  GCTGACATCA  TGATTGGCTT  500

TGCGCGAGGA  GCTCATGGGG  ACTCCTACCC  ATTTGATGGG  CCAGGAAACA  550
```

| | | | | | |
|---|---|---|---|---|---|
| CGCTGGCTCA | TGCCTTTGCG | CCTGGGACAG | GTCTCGGAGG | AGATGCTCAC | 600 |
| TTCGATGAGG | ATGAACGCTG | GACGGATGGT | AGCAGTCTAG | GGATTAACTT | 650 |
| CCTGTATGCT | GCAACTCATG | AACTTGGCCA | TTCTTTGGGT | ATGGGACATT | 700 |
| CCTCTGATCC | TAATGCAGTG | ATGTATCCAA | CCTATGGAAA | TGGAGATCCC | 750 |
| CAAAATTTTA | AACTTTCCCA | GGATGATATT | AAAGGCATTC | AGAAACTATA | 800 |
| TGGAAAGAGA | AGTAATTCAA | GAAAGAAATA | GAAACTT | | 837 |